US010211493B2

(12) United States Patent
Janarthanam et al.

(10) Patent No.: US 10,211,493 B2
(45) Date of Patent: Feb. 19, 2019

(54) THERMAL MANAGEMENT SYSTEM FOR AN ELECTRIFIED VEHICLE

(71) Applicant: FORD GLOBAL TECHNOLOGIES, LLC, Dearborn, MI (US)

(72) Inventors: Suriyaprakash Ayyangar Janarthanam, Westland, MI (US); Bhaskara Boddakayala, Canton, MI (US); Neil Robert Burrows, White Lake Township, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 819 days.

(21) Appl. No.: 14/279,596

(22) Filed: May 16, 2014

(65) Prior Publication Data
US 2015/0333379 A1    Nov. 19, 2015

(51) Int. Cl.
    B60K 11/02     (2006.01)
    H01M 10/63     (2014.01)
    H01M 10/613    (2014.01)
    G01N 11/00     (2006.01)
    H01M 10/48     (2006.01)
    H01M 10/625    (2014.01)
    H01M 10/663    (2014.01)
    H01M 10/6561   (2014.01)
    B60L 1/00      (2006.01)
    B60L 11/18     (2006.01)

(52) U.S. Cl.
    CPC .............. H01M 10/63 (2015.04); B60L 1/003 (2013.01); B60L 11/1874 (2013.01); G01N 11/00 (2013.01); H01M 10/48 (2013.01); H01M 10/486 (2013.01); H01M 10/613 (2015.04); H01M 10/625 (2015.04); H01M 10/6561 (2015.04); H01M 10/663 (2015.04); B60L 2240/445 (2013.01); B60L 2240/525 (2013.01); B60L 2240/545 (2013.01); H01M 2220/20 (2013.01); Y02T 10/7005 (2013.01); Y02T 10/705 (2013.01)

(58) Field of Classification Search
    CPC ................................................. B60K 2001/005
    USPC .............. 180/65.29, 68.4, 68.1, 68.2; 429/62
    See application file for complete search history.

(56) References Cited

U.S. PATENT DOCUMENTS 6,087,028 A * 7/2000 Goto ................. H01M 8/04029
                                                  429/435
6,138,466 A * 10/2000 Lake .................. B60H 1/00278
                                                  429/62
6,186,254 B1 * 2/2001 Mufford .............. B60L 11/1885
                                                  180/165
6,357,541 B1 * 3/2002 Matsuda ................. B60K 6/22
                                                  165/43
6,394,210 B2 * 5/2002 Matsuda ............ B60H 1/00278
                                                  180/65.1

(Continued)

FOREIGN PATENT DOCUMENTS

DE    102011118162 A1    5/2013
EP         2239811 A1    10/2010

(Continued)

Primary Examiner — Jeffrey J Restifo
(74) Attorney, Agent, or Firm — Carlson, Gaskey & Olds

(57) ABSTRACT

A battery system according to an exemplary aspect of the present disclosure includes, among other things, a battery pack, a first sensor at an inlet of the battery pack and a second sensor at an outlet of the battery pack.

15 Claims, 4 Drawing Sheets

(56) References Cited

U.S. PATENT DOCUMENTS

| | | | | |
|---|---|---|---|---|
| 6,450,275 B1* | 9/2002 | Gabriel | ............ | B60K 6/22 165/41 |
| 6,464,027 B1* | 10/2002 | Dage | ............ | B60H 1/004 123/41.14 |
| 6,467,286 B2* | 10/2002 | Hasebe | ............ | B60K 1/02 165/41 |
| 6,481,230 B2* | 11/2002 | Kimishima | ............ | B60H 1/323 62/238.7 |
| 6,651,761 B1* | 11/2003 | Hrovat | ............ | H01M 8/04014 165/41 |
| 6,743,539 B2* | 6/2004 | Clingerman | ...... | H01M 8/04007 123/41.12 |
| 7,284,594 B2* | 10/2007 | Sanada | ............ | F28F 9/002 165/132 |
| 7,823,671 B2* | 11/2010 | Inoue | ............ | B60K 11/02 180/68.1 |
| 7,921,946 B2* | 4/2011 | Kumar | ............ | H01M 10/425 180/65.29 |
| 8,215,432 B2* | 7/2012 | Nemesh | ............ | B60H 1/00278 180/68.1 |
| 8,336,319 B2* | 12/2012 | Johnston | ............ | B60L 3/0046 62/434 |
| 8,402,776 B2 | 3/2013 | Johnston et al. | | |
| 8,448,696 B2 | 5/2013 | Johnston et al. | | |
| 8,839,894 B2* | 9/2014 | Yokoyama | ........ | B60H 1/00385 180/299 |
| 8,919,471 B2* | 12/2014 | Oberti | ............ | B60K 1/00 180/68.4 |
| 2002/0040896 A1* | 4/2002 | Ap | ............ | B60K 1/04 219/208 |
| 2002/0043413 A1* | 4/2002 | Kimishima | ............ | B60H 1/323 180/68.1 |
| 2002/0127448 A1* | 9/2002 | Derflinger | ........ | H01M 8/04029 429/434 |
| 2003/0118891 A1* | 6/2003 | Saito | ............ | B60L 1/003 429/62 |
| 2004/0004461 A1* | 1/2004 | Hamada | ............ | H01M 2/1016 320/112 |
| 2006/0130888 A1* | 6/2006 | Yamaguchi | ............ | F01P 3/20 136/205 |
| 2006/0169507 A1* | 8/2006 | Inoue | ............ | B60K 11/02 180/68.4 |
| 2008/0217080 A1* | 9/2008 | Maier | ............ | B60K 11/02 180/65.31 |
| 2009/0280395 A1* | 11/2009 | Nemesh | ............ | B60H 1/00278 429/62 |
| 2010/0100266 A1* | 4/2010 | Yoshinori | ............ | B60K 1/04 701/22 |
| 2011/0132017 A1* | 6/2011 | Kim | ............ | B60H 1/00278 62/259.2 |
| 2012/0046815 A1* | 2/2012 | Hermann | ............ | B60H 1/00278 701/22 |
| 2012/0085510 A1* | 4/2012 | Kim | ............ | B60K 11/02 165/44 |
| 2012/0152186 A1* | 6/2012 | Sujan | ............ | F01P 3/20 123/41.09 |
| 2012/0247753 A1* | 10/2012 | Bachmann | ......... | B60H 1/00278 165/287 |
| 2013/0118820 A1* | 5/2013 | Yokoyama | ......... | B60H 1/00385 180/65.1 |
| 2013/0183555 A1* | 7/2013 | Boddakayala | ...... | H01M 2/1077 429/72 |
| 2014/0174708 A1* | 6/2014 | Akiyama | ............ | B60R 16/00 165/202 |
| 2014/0216682 A1* | 8/2014 | Cherouat | ............ | B60K 11/02 165/11.1 |
| 2014/0338376 A1* | 11/2014 | Carpenter | ............ | B60L 1/003 62/115 |
| 2015/0101789 A1* | 4/2015 | Enomoto | ........... | B60H 1/00485 165/202 |
| 2015/0103110 A1* | 4/2015 | Shimada | ............ | B41J 11/002 347/12 |
| 2015/0273976 A1* | 10/2015 | Enomoto | ............ | B60K 6/22 165/202 |
| 2015/0333379 A1* | 11/2015 | Janarthanam | ....... | H01M 10/613 429/61 |

FOREIGN PATENT DOCUMENTS

| | | |
|---|---|---|
| JP | 2013107420 A | 6/2013 |
| JP | 2014-000906 A | 1/2014 |
| WO | 2013072744 A1 | 5/2013 |
| WO | 2013076405 A1 | 5/2013 |

\* cited by examiner

THERMAL MANAGEMENT SYSTEM FOR AN ELECTRIFIED VEHICLE

TECHNICAL FIELD

This disclosure relates to a thermal management system, and more particularly, but not exclusively, to a thermal management system configured to infer coolant flow through a vehicle component.

BACKGROUND

Electrified vehicles, such as hybrid electric vehicles (HEV's), plug-in hybrid electric vehicles (PHEV's), battery electric vehicles (BEV's), or fuel cell vehicles differ from conventional engine vehicles in that they are powered by one or more electric machines (i.e., electric motors and/or generators) instead of or in addition to an internal combustion engine. High voltage current for powering the electric machines is typically supplied by a high voltage traction battery pack.

Many electrified vehicles include thermal management systems that manage the thermal demands of various components during vehicle operation, including the high voltage traction battery pack. The thermal management system typically includes various pipes, joints, connectors, etc. that communicate coolant throughout the system. It is desirable to improve the system integrity of the thermal management system.

SUMMARY

A battery system according to an exemplary aspect of the present disclosure includes, among other things, a battery pack, a first sensor at an inlet of the battery pack and a second sensor at an outlet of the battery pack.

In a further non-limiting embodiment of the foregoing system, the first sensor and the second sensor are integrated pressure and temperature sensors.

In a further non-limiting embodiment of either of the foregoing systems, a control module is in electrical communication with the first sensor and the second sensor.

In a further non-limiting embodiment of any of the foregoing systems, the control module is configured to infer flow information of a coolant communicated through the battery pack.

In a further non-limiting embodiment of any of the foregoing systems, the first sensor and the second sensor are configured to indicate a fluid condition of a coolant communicated through the battery pack.

A thermal management system according to another exemplary aspect of the present disclosure includes, among other things, a vehicle component, a first cooling loop that circulates a coolant through the vehicle component, a first sensor configured to indicate a fluid condition of the coolant and a control module configured to monitor the fluid condition to infer flow information of the coolant through the vehicle component.

In a further non-limiting embodiment of the foregoing system, the vehicle component is a battery pack.

In a further non-limiting embodiment of either of the foregoing systems, a second cooling loop circulates a second coolant to a second vehicle component and a third cooling loop circulates a third coolant to a third vehicle component.

In a further non-limiting embodiment of any of the foregoing systems, the vehicle component is a high voltage battery pack, the second vehicle component is at least one of a controller, an inverter and a converter, and the third vehicle component is an engine.

In a further non-limiting embodiment of any of the foregoing systems, the fluid condition includes a pressure or a temperature of the coolant.

In a further non-limiting embodiment of any of the foregoing systems, the first sensor is positioned at an inlet of the vehicle component.

In a further non-limiting embodiment of any of the foregoing systems, a second sensor is positioned at an outlet of the vehicle component.

In a further non-limiting embodiment of any of the foregoing systems, the first sensor is an integrated pressure and temperature sensor.

In a further non-limiting embodiment of any of the foregoing systems, the first sensor is a differential pressure sensor, and including a second sensor and a third sensor that are temperature sensors.

In a further non-limiting embodiment of any of the foregoing systems, a heater is configured to heat the coolant to precondition the vehicle component.

In a further non-limiting embodiment of any of the foregoing systems, at least a radiator and a chiller are disposed within the first cooling loop.

In a further non-limiting embodiment of any of the foregoing systems, the control module is programmed with a lookup table for estimating a flow rate of the coolant based on the fluid condition.

A method according to another exemplary aspect of the present disclosure includes, among other things, sensing a fluid condition associated with a coolant of a thermal management system and monitoring the fluid condition to infer flow information of the coolant through a battery pack.

In a further non-limiting embodiment of the foregoing method, the sensing step is performed with a first sensor positioned at an inlet of the battery pack and a second sensor positioned at an outlet of the battery pack.

In a further non-limiting embodiment of either of the foregoing methods, the flow information is estimated based on pressure and temperature values that are stored in a lookup table.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure relates to a thermal management system for an electrified vehicle. The thermal management system may include a battery pack and one or more sensors configured to indicate a fluid condition of a coolant communicated through the battery pack. For example, the sensor(s) may sense pressures and temperatures of the coolant. A control module monitors the fluid condition to infer a coolant flow through the battery pack. These and other features are discussed in greater detail within this detailed description.

Figure 1:
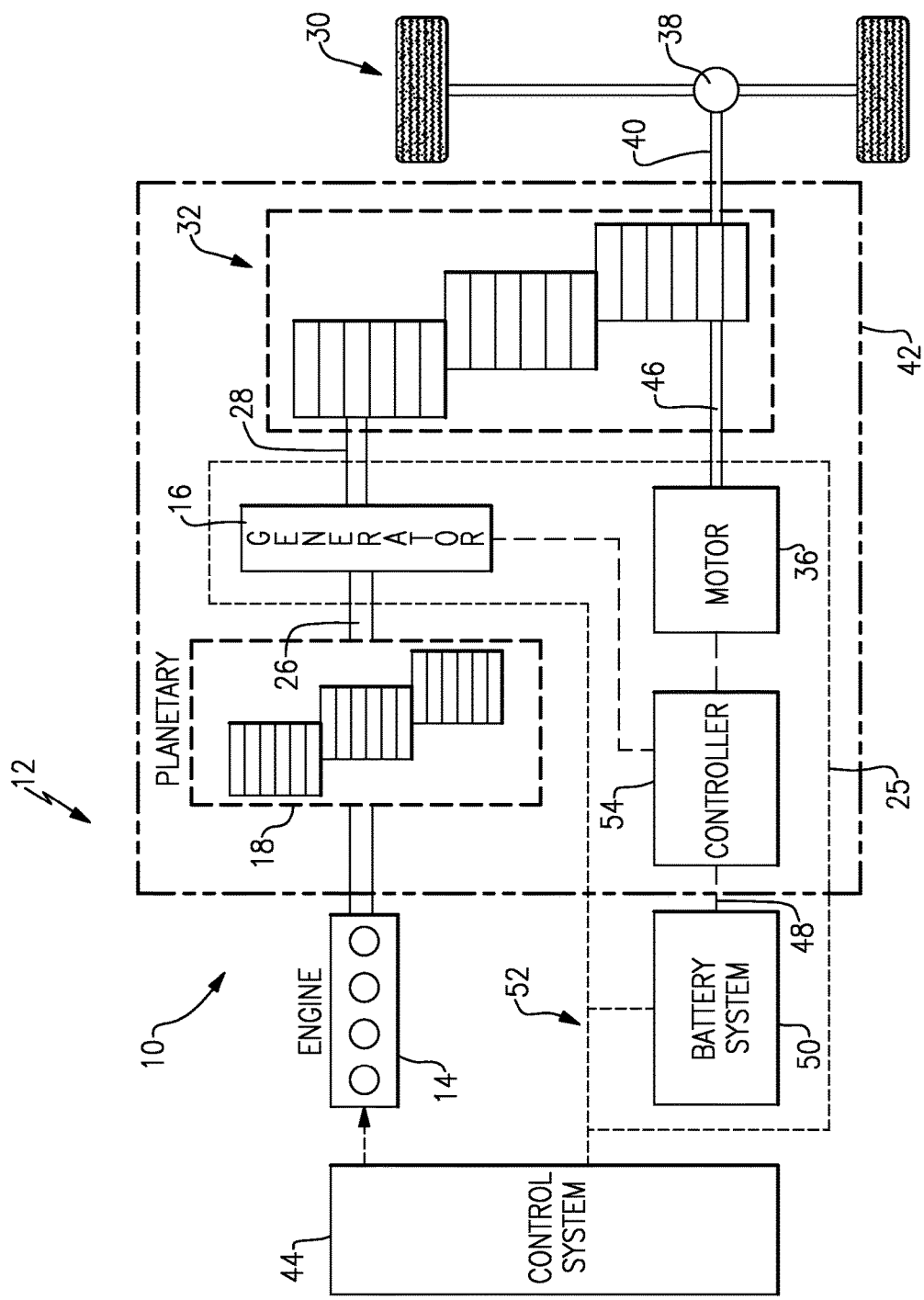
FIG. 1 schematically illustrates a powertrain of an electrified vehicle.

FIG. 1 schematically illustrates a powertrain 10 for an electrified vehicle 12, such as a HEV. Although depicted as a HEV, it should be understood that the concepts described herein are not limited to HEV's and could extend to other electrified vehicles, including but not limited to, PHEV's, BEV's, fuel cell vehicles, or any other alternate fuel vehicles.

In one embodiment, the powertrain 10 is a hybrid drive system that employs a first drive system that includes a combination of an engine 14 and a generator 16 (i.e., a first electric machine), and a second drive system that includes at least a motor 36 (i.e., a second electric machine), the generator 16 and a battery system 50. For example, the motor 36, the generator 16 and the battery system 50 may make up an electric drive system 25 of the powertrain 10. The first and second drive systems generate torque to drive one or more sets of vehicle drive wheels 30 of the electrified vehicle 12, as discussed in greater detail below.

The engine 14, such as an internal combustion engine, and the generator 16 may be connected through a power transfer unit 18. The generator 16 is driven by the power transfer unit 18 when acting as a generator to convert kinetic energy to electrical energy. The generator 16 can alternatively function as a motor to convert electrical energy into kinetic energy, thereby outputting torque to a shaft 26. Because the generator 16 is operatively connected to the engine 14, the speed of the engine 14 can be controlled by the generator 16.

A shaft 28 is connected to vehicle drive wheels 30 through a second power transfer unit 32. The second power transfer unit 32 transfers torque from the engine 14 to a differential 38 to provide traction to the vehicle drive wheels 30. The differential 38 may include a plurality of gears that enable the transfer of torque to the vehicle drive wheels 30. The second power transfer unit 32 is mechanically coupled to an axle 40 through the differential 38 to distribute torque to the vehicle drive wheels 30.

The motor 36 can also be employed to drive the vehicle drive wheels 30 by outputting torque to a shaft 46 that is also connected to the second power transfer unit 32. In one embodiment, the motor 36 and the generator 16 are part of a regenerative braking system in which both the motor 36 and the generator 16 can be employed as motors to output torque. For example, the motor 36 and the generator 16 can each output electrical power to a high voltage bus 48 and the battery system 50. The battery system 50 may include a high voltage battery pack that is capable of outputting electrical power to operate the motor 36 and the generator 16. Other types of energy storage devices and/or output devices can also be incorporated for use with the electrified vehicle 12. The battery system 50 may be made up of one or more battery modules that include battery cells that store the energy necessary to power the motor 36 and/or generator 16.

The motor 36, the generator 16, the power transfer unit 18, and the power transfer unit 32 may generally be referred to as a transaxle 42, or transmission, of the electrified vehicle 12. Thus, when a driver selects a particular shift position, the transaxle 42 is appropriately controlled to provide the corresponding gear for advancing the electrified vehicle 12 by providing traction to the vehicle drive wheels 30.

The powertrain 10 may additionally include a control system 44 for monitoring and/or controlling various aspects of the electrified vehicle 12. For example, the control system 44 may communicate with the electric drive system 25, the power transfer units 18, 32 or other components to monitor and/or control the electrified vehicle 12. The control system 44 includes electronics and/or software to perform the necessary control functions for operating the electrified vehicle 12. In one embodiment, the control system 44 is a combination vehicle system controller and powertrain control module (VSC/PCM). Although it is shown as a single hardware device, the control system 44 may include multiple controllers in the form of multiple hardware devices, or multiple software controllers within one or more hardware devices.

A controller area network (CAN) 52 allows the control system 44 to communicate with the transaxle 42. For example, the control system 44 may receive signals from the transaxle 42 to indicate whether a transition between shift positions is occurring. The control system 44 may also communicate with a battery electronic control module (BECM) of the battery system 50, or other control modules.

Additionally, the electric drive system 25 may include one or more controllers 54, such as an inverter system controller (ISC). The controller 54 is configured to control specific components within the transaxle 42, such as the generator 16 and/or the motor 36, such as for supporting bidirectional power flow. In one embodiment, the controller 54 is an inverter system controller combined with a variable voltage converter (ISC/VVC).

Figure 2:
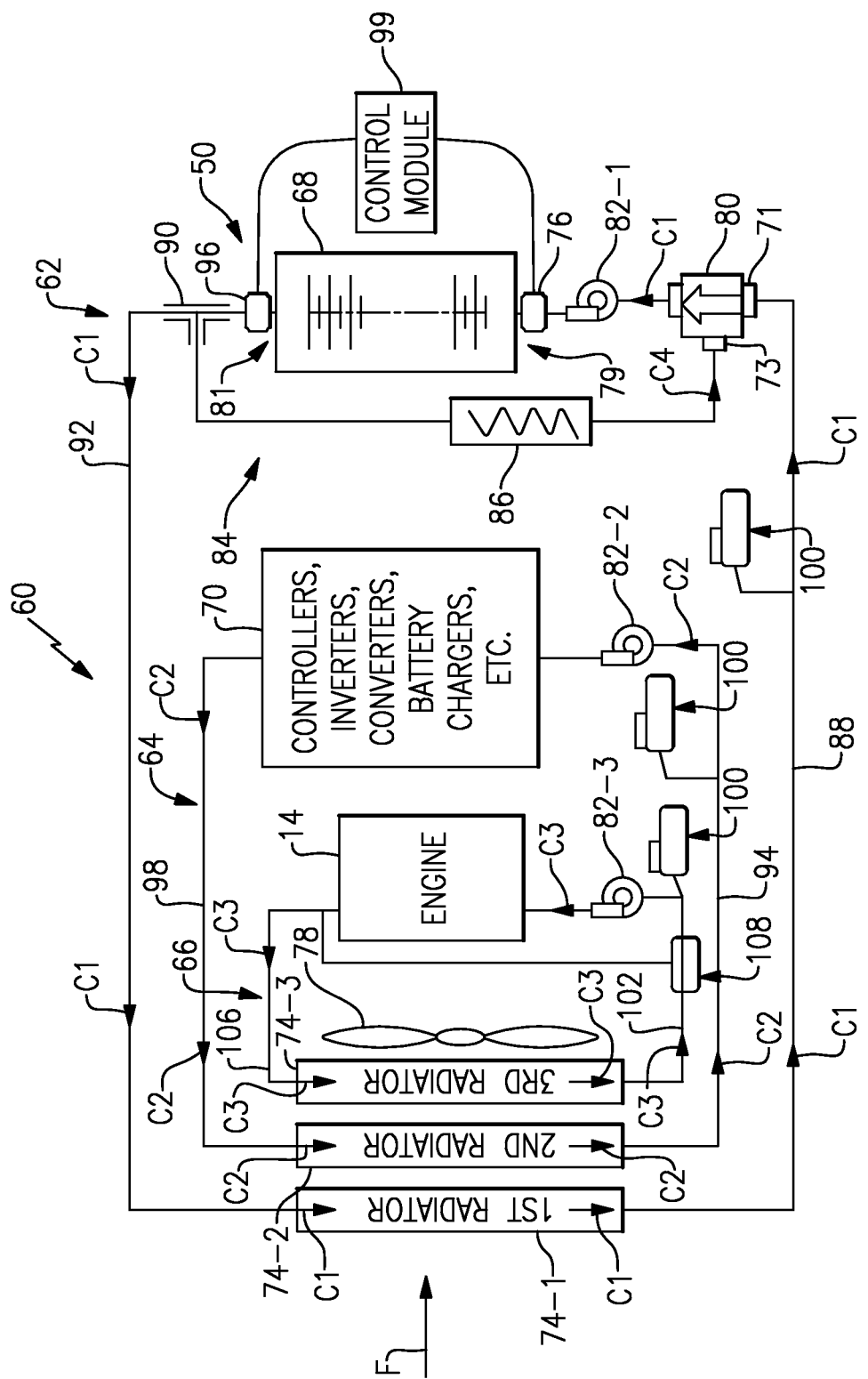
FIG. 2 illustrates a thermal management system according to a first embodiment of this disclosure.

FIG. 2 illustrates a thermal management system 60 that can be incorporated into an electrified vehicle. For example, the thermal management system 60 could be employed by the electrified vehicle 12 of FIG. 1 (or any other electrified vehicle) in order to manage the thermal loads generated by various vehicle components, such as the engine 14, the battery system 50 and/or the controllers 54. The thermal management system 60 can selectively communicate coolant to these components to either cool or heat the components depending on ambient conditions and/or other conditions.

In one embodiment, the thermal management system 60 includes a first cooling loop 62, a second cooling loop 64, and third cooling loop 66. Although three cooling loops are illustrated in this embodiment, the thermal management system 60 could include a greater or fewer number of cooling loops within the scope of this disclosure.

In one non-limiting embodiment, the first cooling loop 62 is configured to supply a coolant C1 to the battery system 50, the second cooling loop 64 is configured to supply a coolant C2 to vehicle components such as various controllers, inverters, converters, battery chargers, etc. (collectively shown at 70), and the third cooling loop 66 can supply a coolant C3 to the engine 14. As illustrated, the coolant C1 of the first cooling loop 62 may be used to thermally manage a battery pack 68 of the battery system 50. Other vehicle components may alternatively or additionally be conditioned by the thermal management system 60. In other words, the first cooling loop 62, the second cooling loop 64, and the third cooling loop 66 can each supply coolant to one or more components.

The coolants C1, C2 and C3 may be a conventional type of coolant mixture, such as water mixed with ethylene glycol. Other coolants could also be used by the thermal management system 60.

The thermal management system 60 may additionally include multiple radiators. For example, a first radiator 74-1 may be incorporated into the first cooling loop 62, a second radiator 74-2 may be incorporated into the second cooling loop 64, and a third radiator 74-3 may be in fluid communication with the third cooling loop 66. The radiators 74-1, 74-2 and 74-3 may be used to cool the coolants C1, C2, and C3 that are supplied to the first cooling loop 62, the second cooling loop 64, and the third cooling loop 66, respectively. In one embodiment, the first radiator 74-1 is a low temperature radiator, the second radiator 74-2 is a mid-temperature radiator, and the third radiator 74-3 is a high temperature radiator.

A radiator fan 78 may be positioned adjacent to the radiators 74-1, 74-2 and 74-3. In one embodiment, the radiator fan 78 is positioned immediately adjacent to the third radiator 74-3. However, other positions are also contemplated.

Multiple pumps may be disposed throughout the thermal management system 60. For example, in one non-limiting embodiment, the first cooling loop 62 includes a first pump 82-1, the second cooling loop 64 includes a second pump 82-2, and the third cooling loop 66 includes a third pump 82-3. The pumps 82-1, 82-2, and 82-3 help circulate the coolants C1, C2, and C3.

The thermal management system 60 may optionally employ one or more degas overflow tanks 100. In this embodiment, degas overflow tanks 100 are incorporated into each of the first cooling loop 62, the second cooling loop 64, and the third cooling loop 66. The degas overflow tanks 100 could be located anywhere within any cooling loop. The degas overflow tanks 100 allow entrained air and gasses in the coolants C1, C2, and C3 to be separated from the coolants as they flow through the degas overflow tanks 100.

In one non-limiting operating mode of the thermal management system 60, the coolant C1 is communicated into the first radiator 74-1, the coolant C2 is communicated into the second radiator 74-2, and the coolant C3 is communicated into the third radiator 74-3. The coolant C1 is supplied to the first cooling loop 62, the coolant C2 is supplied to the second cooling loop 64, and the coolant C3 is supplied to the third cooling loop 66.

The radiator fan 78 draws airflow F through the first radiator 74-1, the second radiator 74-2, and the third radiator 74-3 for undergoing heat transfer with each of the coolants C1, C2, and C3. For example, the airflow F exchanges heat with the coolants C1, C2, and C3 to cool them. Heat is removed into the airflow F prior to communicating the coolants C1, C2, and C3 to the first cooling loop 62, the second cooling loop 64, and the third cooling loop 66, respectively, for cooling the battery pack 68, the various controllers, inverters, converters, battery chargers, etc. (shown at 70), and the engine 14.

In one non-limiting embodiment, the coolant C1 exits the first radiator 74-1 into a line 88 of the first cooling loop 62 and is communicated to a three-way valve 80. The three-way valve 80 may be positioned upstream from the battery pack 68 to control the flow of the coolant C1 through the battery pack 68. The pump 82-1 may be positioned between the three-way valve 80 and the battery pack 68 for circulating the coolant C1 into and through the battery pack 68.

The first cooling loop 62 may additionally include a chiller loop 84. The chiller loop 84 includes a chiller 86 for providing additional cooling to the coolant C1 during certain conditions. For example, when an ambient temperature exceeds a predefined threshold, the three-way valve 80 may close an inlet 71 that connects to the line 88 of the first cooling loop 62 and open an inlet 73 that connects to the chiller loop 84 to provide a chilled coolant C4 to the battery pack 68. In other conditions, the inlet 73 of the three-way valve 80 is closed and the inlet 71 is opened to freely communicate the coolant C1 from the line 88 into the battery pack 68.

A T-joint 90 may be located downstream of the battery pack 68. The T-joint 90 is adapted to split the coolant C1 that exits the battery pack 68 between the chiller loop 84 and a line 92. The line 92 connects back to the first radiator 74-1 to close the first cooling loop 62.

Meanwhile, the coolant C2 may exit the second radiator 74-2 via a line 94 of the second cooling loop 64. The coolant C2 may be communicated to cool the various controllers, inverters, converters, battery chargers, etc., which are indicated at 70 in FIG. 2. The coolant C2 may be returned to the second radiator 74-2 via a line 98.

Finally, the coolant C3 may selectively exit the radiator 74-3 via line 102 of the third cooling loop 66. The coolant C3 is communicated to cool the engine 14. The coolant C3 may be returned to the third radiator 74-3 via line 106 after cooling the engine 14.

The third cooling loop 66 may optionally include a thermostat 108. In one embodiment, the thermostat 108 is a dual stage continuous regulator valve configured to regulate an inlet temperature of the engine 14. The thermostat 108 may close the line 102 of the third cooling loop 66 under certain operating conditions where the engine 14 does not require cooling from the third radiator 74-3. In other words, the thermostat 108 may prevent the communication of the coolant C3 to the engine 14 during certain operating conditions.

As described above, the battery system 50 may be part of the first cooling loop 62 of the thermal management system 60. In this way, the battery system 50 may be used to monitor the flow of the coolant C1 of the first cooling loop 62 through the battery pack 68. For example, the battery system 50 may detect whether a coolant loss is occurring within the battery pack 68 or at some location remote from the battery pack 68.

In one non-limiting embodiment, the battery system 50 includes the battery pack 68, a first sensor 76, a second sensor 96 and a control module 99. The first sensor 76 and the second sensor 96 are in electrical communication with the control module 99. The first sensor 76 may be positioned at an inlet 79 of the battery pack 68, and the second sensor 96 may be positioned at an outlet 81 of the battery pack 68.

In one embodiment, both the first sensor 76 and the second sensor 96 are integrated pressure and temperature sensors. Other sensors may additionally or alternatively be utilized by the battery system 50 to monitor coolant flow of the thermal management system 60.

While schematically illustrated as a single module in the illustrated embodiment, the control module 99 may be part of a larger control system and may be controlled by various other controllers throughout an electrified vehicle, such as a vehicle system controller (VSC) that includes a powertrain control unit, a transmission control unit, an engine control unit, a BECM, etc. It should therefore be understood that the control module 99 and one or more other controllers can collectively be referred to as a "control module" that controls, such as through a plurality of integrated algorithms, various actuators in response to signals from various sensors to control functions associated with a vehicle, and in this case, with the thermal management system 60. The various controllers that make up the VSC can communicate with one another using a common bus protocol (e.g., CAN). In one non-limiting embodiment, the control module 99 may be part of a BECM of the battery system 50.

In one embodiment, the first sensor 76 and the second sensor 96 may indicate (i.e., sense) a fluid condition associated with the coolant C1. The fluid condition may include the pressure and temperature of the coolant C1. The pressure and temperature values sensed by the first sensor 76 and the second sensor 96 can be communicated to the control module 99 for monitoring pressure and temperature differentials of the coolant C1 between the inlet 79 and the outlet 81 of the battery pack 68. Based on these pressure and temperature differentials, the control module 99 can infer a coolant flow rate of the coolant C1 through the battery pack 68.

For example, the pressure and temperature information sensed by the first sensor 76 and the second sensor 96 may change if leakages and blockages occur within the thermal management system 60, either from within the battery pack 68 or outside of the battery pack 68. Any variations or reductions of coolant pressure or temperature between the inlet 79 and the outlet 81 of the battery pack 68 may indicate issues in the thermal management system 60 outside or inside of the battery pack 68. Sensed pressure variations could be due to blocked pipe lines or leakage in the thermal management system 60, or degraded performance of one of the pumps 82-1, 82-2, 83-3. Alternatively, a rise in the temperature of the coolant C1 between the inlet 79 and the outlet 81 of the battery pack 68 may indicate a malfunction of the chiller 86, improper coolant circulation, deficiencies of the radiator fan 78, or other problems.

The control module 99 monitors any pressure or temperature differentials across the battery pack 68 between the inlet 79 and the outlet 81. In one embodiment, based on calibrated threshold values, which may be stored in a lookup table in memory of the control module 99, the control module 99 can infer a flow rate of the coolant C1 that is communicated through the battery pack 68 and then take necessary remedial actions per a given control strategy. In other words, for a given temperature and pressure, the coolant C1 will have a known flow rate which can be determined from the lookup table. The control module 99 can determine if any remedial actions are necessary based on this flow rate information.

In another embodiment, the control module 99 can also calculate a heat rejection rate of the coolant C1 using temperature values sensed by the first sensor 76 and/or the second sensor 96. These temperature values can be utilized to monitor thermal performance of the battery pack 68 for given charge/discharge power. This information can provide insight into battery cell aging.

Monitoring the pressure and temperature of the battery pack 68 in this manner can also eliminate any suspicion on the thermal management system 60 where excessive temperature rises are observed within the battery pack 68 between the inlet 79 and the outlet 81. For example, if the pressure and temperature values of the coolant C1 are not within a predefined range (when referenced against the lookup table), then any temperature rise can be pinpointed to an internal issue of the battery pack 68.

In another embodiment, the control module 99 may determine whether to open the inlet 71 or the inlet 73 of the three-way valve 80 in response to pressure and temperature information from the first sensor 76 and/or the second sensor 96. For example, temperature readings of the first sensor 76 can be used to switch between communicating the coolant C1 from the first radiator 74-1 and communicating the coolant C4 from the chiller loop 84.

Figure 3:
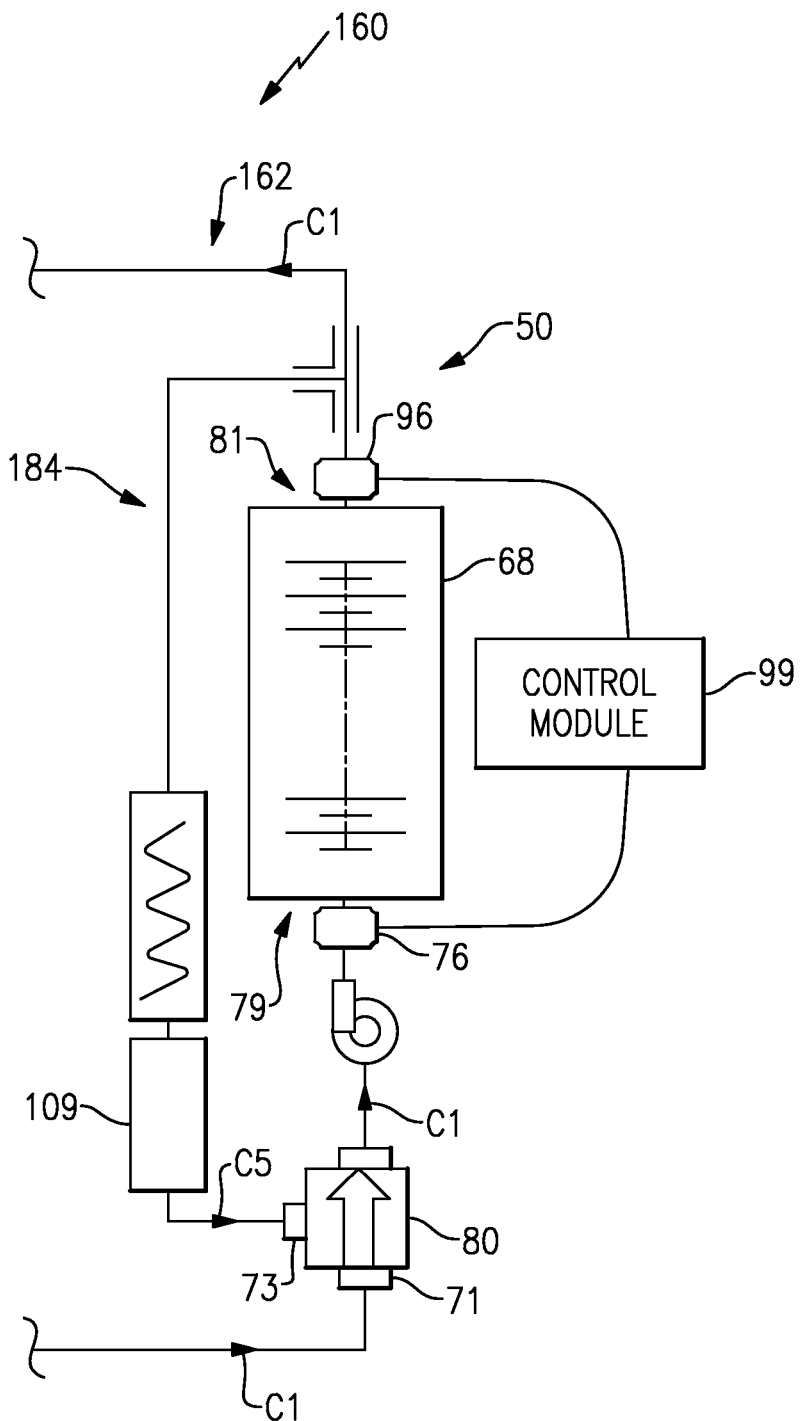
FIG. 3 illustrates a thermal management system according to a second embodiment of this disclosure.

FIG. 3 illustrates select portions of another exemplary thermal management system 160. In this disclosure, like reference numbers designate like elements where appropriate and reference numerals with the addition of 100 or multiples thereof designate modified elements that are understood to incorporate the same features and benefits of the corresponding original elements.

In this embodiment, the thermal management system 160 includes a cooling loop 162. Of course, the thermal management system 160 could include additional cooling loops (see, for example, the multiple cooling loops of the thermal management system 60 of FIG. 2).

The cooling loop 162 is similar to the first cooling loop 62 of FIG. 2. However, in this embodiment, a chiller loop 184 of the cooling loop 162 includes a heater 109. The heater 109 can be used to precondition the battery pack 68, such as for cold climate applications.

In one embodiment, the heater 109 is a positive temperature coefficient heater. In another embodiment, the heater 109 is a glow plug type heater. Other heaters are also contemplated for use within the thermal management system 160.

In one non-limiting embodiment, the heater 109 heats a coolant C1 that is circulated through the cooling loop 162 to thermally manage the battery pack 68. When heating is desired, the inlet 71 of the three-way valve 80 may be closed and the inlet 73 opened to communicate a heated coolant C5 to the battery pack 68.

The first sensor 76 and the second sensor 96 of the battery system 50 may be used to indicate whether coolant has reached a preconditioned temperature. The heater 109 can be turned "off" if the control module 99 determines no heat transfer has occurred between the coolant C1 and the battery pack 68 (i.e., the temperature of the coolant C1 at the inlet 79 of the battery pack 68 is equal to the temperature of the coolant C1 at the outlet 81).

The control module 99 can also monitor the feedback from the first sensor 76 and the second sensor 96 to determine a flow rate of the coolant C1. Stated another way, the control module 99 can confirm flow of the coolant C1 when the heater 109 is turned "on" to avoid overheating of the coolant C1.

Figure 4:
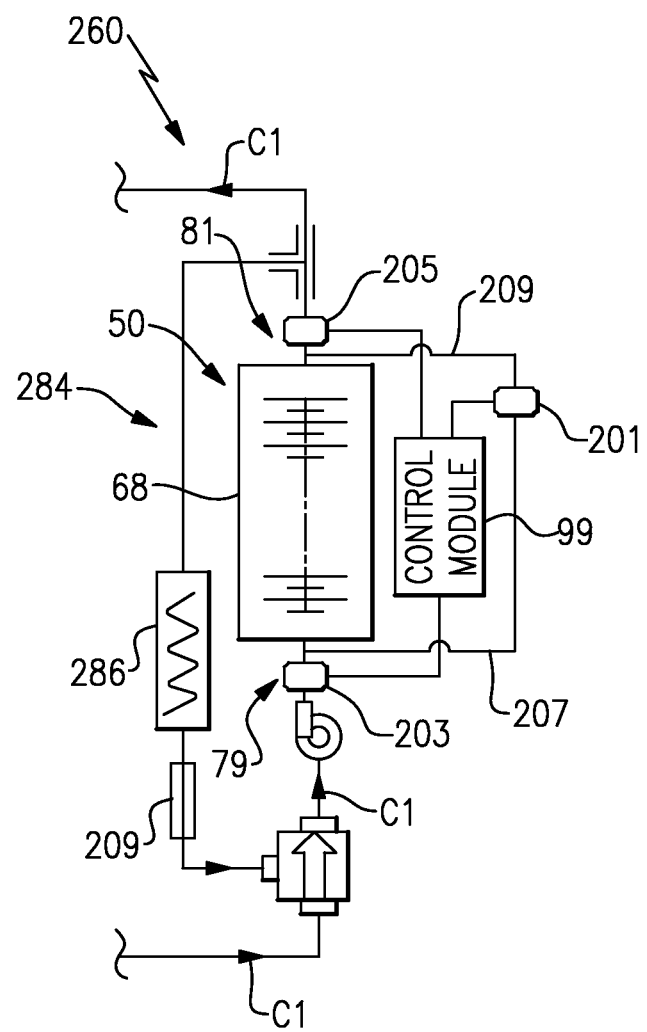
FIG. 4 illustrates a thermal management system according to yet another embodiment of this disclosure.

FIG. 4 illustrates yet another exemplary thermal management system 260. In this embodiment, the thermal management system 260 includes a first sensor 201, a second sensor 203, and a third sensor 205 for monitoring a battery system 50 that includes a battery pack 68. In one embodiment, the first sensor 201 is a differential pressure sensor and the second sensor 203 and the third sensor 205 are temperature sensors.

The first sensor 201 may include a first lead 207 positioned near an inlet 79 of the battery pack 68 and a second lead 209 positioned near an outlet 81 of the battery pack 68. In one embodiment, the second sensor 203 is positioned at the inlet 79, and the third sensor 205 is positioned at the outlet 81.

The first sensor 201, the second sensor 203, and the third sensor 205 are in electrical communication with a control module 99. Pressure values sensed by the first sensor 201 and temperature values sensed by the second and third sensors 203, 205 can be communicated to the control module 99 for monitoring any pressure and temperature differentials of a coolant C1 between the inlet 79 and the outlet 81 of the battery pack 68. Based on these pressure and temperature differentials, the control module 99 can infer a coolant flow rate of the coolant C1 through the battery pack 68.

The thermal management system 260 may additionally include a chiller loop 284 that includes a chiller 286 and a heater 209 for either selectively cooling or heating the coolant C1 during certain conditions. In other words, the thermal management system 260 can be implemented for use in either hot or cold environments.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A thermal management system, comprising:
   a vehicle component;
   a first cooling loop that circulates a coolant through said vehicle component;
   a first sensor positioned at an inlet of said vehicle component and configured to indicate a fluid condition of said coolant;
   a second sensor positioned at an outlet of said vehicle component;
   a third sensor adapted to indicate a different fluid condition than either of said first sensor or said second sensor and including a first lead positioned near said inlet and a second lead positioned near said outlet; and
   a control module configured to monitor said fluid condition to infer flow information of said coolant through said vehicle component.

2. The system as recited in claim 1, wherein said vehicle component is a battery pack.

3. The system as recited in claim 1, comprising a second cooling loop that circulates a second coolant to a second vehicle component and a third cooling loop that circulates a third coolant to a third vehicle component.

4. The system as recited in claim 3, wherein said vehicle component is a high voltage battery pack, said second vehicle component is at least one of a controller, an inverter and a converter, and said third vehicle component is an engine.

5. The system as recited in claim 1, wherein said fluid condition includes a pressure or a temperature of said coolant.

6. The system as recited in claim 1, wherein said first sensor is an integrated pressure and temperature sensor.

7. The system as recited in claim 1, wherein said third sensor is a differential pressure sensor, and said first and second sensors are temperature sensors.

8. The system as recited in claim 1, comprising a heater configured to heat said coolant to precondition said vehicle component.

9. The system as recited in claim 1, comprising at least a radiator and a chiller disposed within said first cooling loop.

10. The system as recited in claim 1, wherein said control module is programmed with a lookup table for estimating a flow rate of said coolant based on said fluid condition.

11. A thermal management system, comprising:
    a first cooling loop including a low temperature radiator;
    a battery pack thermally managed by said first cooling loop;
    a second cooling loop including a mid-temperature radiator;
    a vehicle component including a vehicle component including controller, an inverter, a converter, or a charger thermally managed by said second cooling loop;
    a third cooling loop including a high temperature radiator; and
    an engine thermally managed by said third cooling loop.

12. The system as recited in claim 11, comprising a control module configured to infer a flow rate of coolant communicated within said first cooling loop.

13. The system as recited in claim 12, wherein said control module is configured to determine whether remedial action is necessary based on said flow rate.

14. The system as recited in claim 11, wherein each of said first cooling loop, said second cooling loop, and said third cooling loop includes a pump and a degas overflow tank.

15. A thermal management system, comprising:
    a first cooling loop including a first radiator;
    a battery pack thermally managed by said first cooling loop;
    a second cooling loop including a second radiator;
    a vehicle component thermally managed by said second cooling loop;
    a third cooling loop including a third radiator;
    an engine thermally managed by said third cooling loop, and wherein the first cooling loop includes a three-way valve positioned upstream from said battery pack and a T-joint positioned downstream from said battery pack.

* * * * *

UNITED STATES PATENT AND TRADEMARK OFFICE
CERTIFICATE OF CORRECTION

| | |
|---|---|
| PATENT NO. | : 10,211,493 B2 |
| APPLICATION NO. | : 14/279596 |
| DATED | : February 19, 2019 |
| INVENTOR(S) | : Suriyaprakash Ayyangar Janarthanam, Bhaskara Boddakayala and Neil Roberts Burrows |

Page 1 of 1

It is certified that error appears in the above-identified patent and that said Letters Patent is hereby corrected as shown below:

In the Claims

In Claim 11, Column 10, Lines 23-24; remove redundant recitation of "vehicle component including."

Signed and Sealed this
Twenty-fifth Day of June, 2019

Andrei Iancu
*Director of the United States Patent and Trademark Office*